United States Patent [19]

Peel et al.

[11] 3,984,429

[45] Oct. 5, 1976

[54] PHARMACEUTICALLY ACTIVE COMPOUNDS

[75] Inventors: Mervyn Evan Peel; Alexander William Oxford, both of London, England

[73] Assignee: Allen & Hanburys Limited, London, England

[22] Filed: Dec. 5, 1974

[21] Appl. No.: 530,038

Related U.S. Application Data

[63] Continuation of Ser. No. 193,971, Oct. 29, 1971, abandoned.

[30] Foreign Application Priority Data

Nov. 27, 1970 United Kingdom............... 56465/70

[52] U.S. Cl............................................. 260/308 D
[51] Int. Cl.²...................................... C07D 257/04
[58] Field of Search................. 260/308 D; 193/971

[56] References Cited

OTHER PUBLICATIONS

Chem. Abstracts, vol. 66, 36740t, (1967).
J. Org. Chem., vol. 24, 1464–1467, (1959).
J. Med. Chem., vol. 11, 111–117, (1968).

Primary Examiner—Frederick E. Waddell
Attorney, Agent, or Firm—Bacon & Thomas

[57] ABSTRACT

Compounds of the general formula:

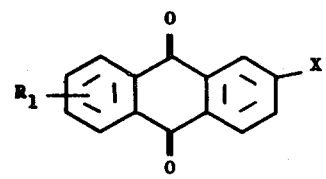

wherein X represents a 5-[1H]-tetrazolyl group, $R_1$ represents a hydrogen atom, a halogen atom, a hydroxyl group or a group —$OR_2$, (in which $R_2$ may be a lower alkyl or alkenyl group containing from 1 to 6 carbon atoms optionally substituted by one or more hydroxy groups, an aryl group, an aryloxy group, an alkoxy group or a dialkylamino group) or a group —$NR_3R_4$, in which $R_3$ and $R_4$ which may be the same or different, represent a hydrogen atom, a lower alkyl group containing from 1 to 6 carbon atoms, optionally substituted by a hydroxy group, or $R_3$ and $R_4$ together with the nitrogen atom may form a ring which may optionally be substituted with another heteroatom and pharmaceutically acceptable salts thereof.

These compounds have useful immunological activity and inhibit the release of spasmogen mediators.

8 Claims, No Drawings

PHARMACEUTICALLY ACTIVE COMPOUNDS

This is a continuation of application Ser. No. 193,971, filed Oct. 29, 1971 now abandoned.

This invention relates to novel anthraquinone derivatives, to processes for the preparation thereof and to compositions containing such derivatives.

In copending application of Alexander W. Oxford et al filed July 19, 1971 entitled "Anthraquinone derivatives" and assigned to a common assignee we have described and claimed anthraquinone derivatives of the general formula I:

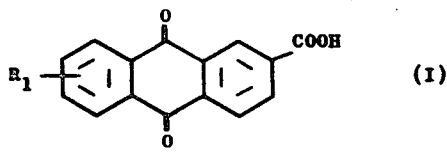

and pharmaceutically acceptable salts and esters thereof, wherein $R_1$ represents a halogen atom, a hydroxyl group or a group $-OR_2$, (in which $R_2$ may be a lower alkyl group containing from 1 to 6 carbon atoms optionally substituted by a hydroxy group, an aryl group, an aryloxy group, an alkoxy group or a dialkylamino group) or a group $-NR_3R_4$, (in which $R_3$ and $R_4$ which may be the same or different, represent a hydrogen atom, a lower alkyl group containing from 1 to 6 carbon atoms, optionally substituted by a hydroxy group, or $R_3$ and $R_4$ together with the nitrogen atom may form a ring which may optionally be substituted with another heteroatom); with the proviso that when $R_1$ is a halogen atom or a methoxy group mixtures of positional isomers produced by existing chemical processes are excluded.

These compounds have useful immunological activity and in particular inhibit the release of spasmogens that normally occurs when a reaginic antibody combines with an antigen.

We have found that related compounds of the formula II below have the same type of pharmacological activity.

According to the present invention there are provided anthraquinone derivatives of general formula II:

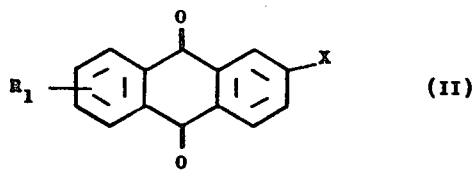

wherein X represents a 5-[1H]-tetrazolyl group; and $R_1$ represents a hydrogen atom, a halogen atom, a hydroxyl group or a group $-OR_2$ (in which $R_2$ may be a lower alkyl or alkenyl group containing from 1 to 6 carbon atoms, optionally substituted by one or more hydroxy groups, an aryl group, an aryloxy group, an alkoxy group or a dialkylamino group) $R_1$ may also represent the group $-NR_3R_4$, in which $R_3$ and $R_4$, which may be the same or different represent a hydrogen atom or a lower alkyl group containing from 1 to 6 carbon atoms optionally substituted by a hydroxy group, or $R_3$ and $R_4$ together with the nitrogen atom may form a ring which may optionally be substituted by another invention, e.g. piperidino, morpholino or N-methylpiperazino.

The invention also includes salts, for example those with alkali metals such as sodium, with organic bases such as dimethylamino ethanol, and with mineral and organic acids, such as those described in the Examples.

The compounds according to the invention have the property of inhibiting the release of spasmogen mediators in the antigen-antibody reaction. Thus, for example 5-[7-(2-hydroxyethoxy)-anthraquinone-2-yl]-1H-tetrazole has been found to be about thirty times as active as disodium cromoglycate in inhibiting the passive cutaneous anaphylaxis (PCA) reaction in the rat using the nematode Nippostrongylis brasiliensis as the antigen (Ogilvie, Brit. J. Immunol., 1967, 12 (2) 113–131).

The use of the compounds is therefore indicated in the treatment of any condition in which an extrinsic antigen combination with antibody is primarily responsible as, for example, in allergic asthma, hay fever, urticaria, eczema, or atopic dermatitis.

Preferred compounds according to the invention are those the preparation of which is described in the Examples.

The invention further provides pharmaceutical compositions comprising a compound according to the invention in association with a pharmaceutically acceptable carrier.

The compounds according to the invention, may be formulated for use as pharmaceutical compositions in the conventional manner with the aid of carriers or excipients and formulatory agents as required and with or without supplementary medicinal agents. Oral administration is most convenient in the form of tablets which may be coated, pastes, aqueous or oily suspensions, solutions, emulsions, or capsules. Carriers include inert diluents such as calcium carbonate and/or disintegrating agents such as alginic acid or starch. Magnesium stearate may be used as a lubricating agent and flavouring or sweetening agents include sucrose, dextrose, glucose, glycerol etc. For emulsions and suspending agents such as sodium carboxymethyl cellulose may be used. Injections may be formulated with the aid of physiologically acceptable carriers and agents as solutions, or as dry products for reconstitution before use. For administration by inhalation the compositions according to the invention may conveniently be in the form of an aerosol spray presentation including both pressurized cans and nebulisers. The dosage at which the active ingredient is administered may vary within a wide range. A suitable oral dosage range is generally from 5 to 500 mg. The pharmaceutical compositions may, with advantage, be formulated to provide a dose within this range either as a single unit or a number of units. In the use of an aerosol the dosage unit may be determined by providing a metering valve in the aerosol pack so that it delivers a metered amount on use. Such a metered amount may be of the order of 1–10 mg. The compositions may be presented in combination with a bronchodilator as required.

The compounds according to the invention may be prepared by treatment of compounds of formula II, in which X represents a $-CN$ group, that is to the corresponding nitriles with hydrazoic acid or its salts with inorganic or organic bases. The reaction can conveniently be carried out with sodium or ammonium azide in an inert solvent, e.g. dimethylformamide, preferably at elevated temperatures, e.g. 100°–130°C.

The parent nitriles may conveniently be prepared from the corresponding carboxylic acids by standard methods of chemistry well known to those skilled in the art, for example the conversion may be effected by dehydration of the corresponding amide (Formula II, X = CONH$_2$) with for example, p-toluenesulphonyl chloride in a mixture of pyridine and dimethylformamide.

The parent acid X = COOH may be prepared by the processes described in our said cognate copending Application Ser. Nos. 37724/70 and 37725/70.

It is understood that the conversion of any of the groups (R$_1$ = Hal) into the groups (R$_1$ = —OR$_2$, —NR$_5$R$_6$) can be effected at any convenient time in the above process.

The following Examples illustrate the invention:

EXAMPLE 1

5-(Anthraquinon-2-yl)-1H-tetrazole 9,10-Dihydro-9,10-dioxo-2-anthroic acid (1008 g), phosphorus pentachloride (915 g) and xylene (8 l) were warmed to reflux and kept at this temperature for 2 hours. About 4 l of a mixture of a phosphorus oxychloride and xylene was distilled off and the remainder of the reaction mixture was, cooled and diluted with benzene (3 l). The solution was added in portions (100 ml) over 1 hour with stirring to ammonia solution (S.G. 0.88) (7 l) and the resulting slurry was warmed for a further 1 hour. The precipitate was filtered off, washed with methanol, and recrystallized from dimethylformamide containing a little dimethylaminoethanol to give 9,10-dihydro-9,10-dioxo-2-anthramide (792 g), m.p. 299°. crystallisation from acetic acid gave material m.p. 304 –5°.

The above amide (251 g), pyridine (1 l), and dimethylformamide (1 l) was heated with tosyl chloride (229 g) for 4 hours at 90°C. The solution was diluted with water and acidified with conc. hydrochloric acid. The precipitate was well washed with water and dried to give 9,10-dihydro-9,10-dioxo-2-anthrocarbonitrile (233 g), m.p. 212 –4°C.

This nitrile (525 g), sodium azide (175 g), ammonium chloride (122 g) and dimethylformamide were stirred for 3 hours at 100°–110°C and the mixture was poured into water (4.5 l) containing 2N hydrochloric acid (1350 ml). The crude precipitate was washed with ethanol and then with water to give 5-(anthraquinon-2-yl)-1H-tetrazole (645 g), m.p. 263–5°C (d).

Dimethylaminoethanol salt

The tetrazole (640 g) was heated with methanol (1250 ml) and dimethylaminoethanol (240 g). The dimethylamino methanol salt (591 g) m.p. 210°–213° (d), separated on cooling.

Sodium salt

The dimethylamino ethanol salt (668 g) was heated in ethanol (8 l) and solution was effected by adding dimethylaminoethanol (90 ml.). A solution of sodium (46.2 g) in ethanol (1600 ml) was added as quickly as possible with vigorous stirring. The precipitate was filtered, washed with ethanol, and dried at 50°C to give the sodium salt monohydrate (546 g), m.p. 300°C.

EXAMPLE 2

5-(7-Methoxy-anthraquinon-2-yl)-1H-tetrazole 9,10-Dihydro-7-methoxy-9,10-dioxo-2-anthroic acid (0.56 g), p-toluenesulphonamide (0.36 g) and phosphorus pentachloride (0.87 g) were heated to 160°–170°C for 1 hour and the phosphorus oxychloride was allowed to distill off as formed. The mixture was cooled and pyridine (1 ml), followed cautiously by water (5 ml), was added. The precipitate was collected, stirred for 90 minutes with 2N sodium hydroxide (10 ml), and filtered. The solid was taken up in benzene/ethyl acetate and filtered through a short column of alumina. Addition of light petroleum (bp 60°–80°) to the eluate gave crystals of 9,10-dihydro-7-methoxy-9,10-dioxo-2-anthrocarbonitrile (0.2 g), m.p. 258°–260°C.

The above nitrile (0.17 g), sodium azide (0.1 g), ammonium chloride and dimethylformamide (20 ml) were heated at 120° for 0.5 hours and then diluted with 2N hydrochloric acid. The precipitate was recrystallised from dimethylformamide/ethyl acetate to give 5-(7-methoxy-anthraquinon-2-yl)-1H-tetrazole (0.12 g), m.p. 265–6°.

EXAMPLE 3

1-[7-(1H-tetrazol-5-yl)-anthraquinon-2-yl]morpholine

7-Fluoro-9,10-dihydro-9,10-dioxo-2-anthroic acid (15 g), phosphorus pentachloride (12 g) and xylene (300 ml) were heated for 15 minutes at 100°–130° till a clear solution was obtained. This was concentrated to small volume and allowed to crystallise. The product was washed with light petroleum (bp 40°–60°) to give 7-fluoro-9,10-dihydro-9,10-dioxo-2-anthroyl chloride (14 g).

Ammonia was bubbled through a stirred solution of the above acid chloride (14 g) in methylene chloride (500 ml) for 2 hours. The precipitate was washed with water and crystallised from acetic acid to give 7-fluoro-9,10-dihydro-9,10-dioxo-2-anthramide (11 g), m.p. 322–3°C.

This amide (11 g) was stirred in refluxing xylene (300 ml) with phosphorus pentoxide (15 g) until only a small amount of gum was present in a clear solution. The solution was decanted and allowed to crystallise to give 7-fluoro-9,10-dihydro-9,10-dioxo-2-anthrocarbonitriel (7 g), m.p. 286–8°C.

The above nitrile (1 g), morpholine (2 g) and dimethylformamide (100 ml) was heated at 90° for 1 hour and water (10 ml) was added. The solution crystallised on cooling to give 1-(7-cyano-anthraquinon-2-yl)morpholine (1.1 g), m.p. 299°–300°C after crystallisation from acetic acid/dimethylformamide.

This nitrile (1 g), sodium azide (0.22 g), ammonium chloride (0.19 g) and dimethylformamide (100 ml) were heated for 11 hours at 125°, further portions of sodium azide (0.22 g) and ammonium chloride (0.19 g) being added after 5 and 10 hours. The mixture was cooled, filtered, and acidified with 2N hydrochloric acid (100 ml). The precipitate was crystallised from aqueous dimethylformamide to give 1-[7-(1H-tetrazol-5-yl)-anthraquinon-2-yl]morpholine (0.5 g), m.p. 303°–304°C.

EXAMPLE 4

1-[7-(1H-Tetrazol-5-yl)-anthraquinon-2-yl]piperidine

7-Fluoro-9,10-dihydro-9,10-dioxo-2-anthrocarbonitrile (1 g), piperidine (2 g), and dimethylformamide (100 ml) were heated at 90° for 1 hour and diluted with water (100 ml). The precipitate was crystallised from dimethylformamide/ethyl acetate to give 1-(7-cyano-anthraquinon-2-yl)-piperidine (1 g), m.p. 274–5°C.

The above nitrile (1 g) was treated with sodium azide (0.66 g) and ammonium chloride (0.57 g) as in the preceding example to give 1-[7(1H-tetrazol-5-yl)-anthraquinon-2-yl]piperidine (0.8 g), m.p. 297–8°C, after crystallisation from dimethylformamide/acetic acid.

EXAMPLE 5

5-[7-(2-Hydroxyethoxy)-anthraquinon-2-yl]-1H-tetrazole

7-Fluoro-9,10-dihydro-9,10-dioxo-2-anthrocarbonitrile (0.9 g) ethylene glycol (5 g) and dimethylformamide were stirred at 0°C and sodium hydride (0.32 g) (50% suspension in oil) was added portionwise over 2 hours. The mixture was diluted with water and the precipitate was collected and dried. The crude product was heated at 120°C for 6 hours with sodium azide (0.6 g) and ammonium chloride (0.5 g) in dimethylformamide (100 ml).

The mixture was diluted with water and acidified. The precipitate was taken up in warm aqueous 8% sodium bicarbonate, filtered, and reacidified. Crystallisation from dimethylformamide acetic acid-water gave 5-[7-(2-hydroxyethoxy)-anthraquinon-2-yl]-1H-tetrazole (0.4 g) m.p. 259.5°–261.5°C.

What is claimed is:

1. A compound of the formula

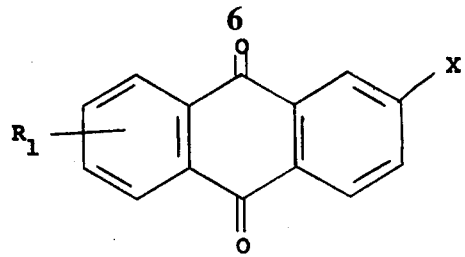

wherein:
X is 5-[1H]-tetrazolyl, and
R₁ is hydrogen or OR₂,
where R₂ is lower alkyl containing up to 6 carbon atoms or lower alkyl containing up to 6 carbon atoms substituted by one or more hydroxy groups; or a pharmaceutically acceptable salt thereof.

2. The compound of claim 1 wherein R₁ is OR₂.

3. The compound of claim 1 which is 5-(anthraquinon-2-yl)-1H-tetrazole or a pharmaceutically acceptable salt thereof.

4. The dimethylaminoethanol salt of the compound of claim 3.

5. The sodium salt of the compound of claim 3.

6. A compound selected from the group consisting of 5-(Anthraquinon-2-yl)-1H-tetrazole dimethylaminoethanol salt, 5-(7-methoxy-anthraquinon-2-yl)-1H-tetrazole, and 5-[7-(2-hydroxyethoxy) anthraquinon-2-yl]-1H-tetrazole.

7. The compound of claim 6 which is 5-(7-Methoxyanthraquinon-2-yl)-1H-tetrazole.

8. The compound of claim 6 which is 5-[7-(2-Hydroxyethoxy) anthraquinon-2-yl]-1H-tetrazole.

* * * * *